United States Patent
Carniel et al.

(10) Patent No.: US 9,492,524 B2
(45) Date of Patent: Nov. 15, 2016

(54) PLAGUE VACCINE

(75) Inventors: Elisabeth Carniel, Issy les Moulineaux (FR); Christian Demeure, Verrieres le Buisson (FR); Anne Derbise, Vitry sur Seine (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 14/419,925

(22) PCT Filed: Aug. 7, 2012

(86) PCT No.: PCT/IB2012/001609
§ 371 (c)(1),
(2), (4) Date: Feb. 5, 2015

(87) PCT Pub. No.: WO2014/023992
PCT Pub. Date: Feb. 13, 2014

(65) Prior Publication Data
US 2015/0202275 A1    Jul. 23, 2015

(51) Int. Cl.
*A61K 39/02* (2006.01)
*C12N 1/36* (2006.01)
*A61K 39/00* (2006.01)

(52) U.S. Cl.
CPC ............ *A61K 39/0291* (2013.01); *C12N 1/36* (2013.01); *A61K 2039/522* (2013.01); *A61K 2039/523* (2013.01); *A61K 2039/542* (2013.01)

(58) Field of Classification Search
None
See application file for complete search history.

(56) References Cited

PUBLICATIONS

Rosenzweig et al. Appl Microbiol Biotechnol (2011) 91:265-286.*
Derbise A, Cerda Mahn A, Ave P, Blisnick T, Huerre M, et al. (2012) An Encapsulated Yersinia pseudotuberculosis Is a Highly Efficient Vaccine against Pneumonic Plague. PLoS Negl Trop Dis 6(2): e1528. doi:10.1371/journal.pntd.0001528.
Chain, P.S.G., et al., "nsights into the evolution of Yersinia pestis through whole-genome comparison with Yersinia pseudotuberculosis," PNAS, vol. 101, No. 38, pp. 13826-13831 (2004).
Derbise, A., et al., "A rapid and simple method for inactivating chromosomal genes in Yersinia," FEMS Immunology and Medical Microbiology, vol. 38, pp. 113-116 (2003).
Derbise, A., et al., "An Encapsulated Yersinia pseudotuberculosis Is a Highly Efficient Vaccine against Pneumonic Plague," PLoS Negl Trop Dis 6(2): e1528. doi:10.1371/journal.pntd.0001528 (2012).
Pouillot, F., et al., "Evaluation of O-antigen inactivation on Pla activity and virulence of Yersinia pseudotuberculosis harbouring the pPla plasmid," Microbiology, vol. 151, pp. 3759-3768 (2005).

* cited by examiner

*Primary Examiner* — Oluwatosin Ogunbiyi
(74) *Attorney, Agent, or Firm* — Law Office of Salvatore Arrigo and Scott Lee, LLP (57) ABSTRACT

The application relates to a *Yersinia pseudotuberculosis* cell, which comprises nucleic acid coding for expression of at least one *Yersinia pestis* Caf1 polypeptide or of at least one antigenic fragment of *Yersinia pestis* Caf1, more particularly to an attenuated *Y. pseudotuberculosis* cell, which expresses the *Y. pestis* capsule. Said *Y. pseudotuberculosis* cell is exceptionally efficient in protecting against both bubonic plague and pulmonary plague.

19 Claims, 5 Drawing Sheets

*Y. pseudotuberculosis*     *Y. pestis*

V674     V674TnF1     CO92

⇐ ⇐ F1 signal

FIGURE 3

V674pF1     V674TnF1

PLAGUE VACCINE

SEQUENCE LISTING

The instant application contains a Sequence Listing which has been submitted electronically in ASCII format and is hereby incorporated by reference in its entirety. Said ASCII copy, created on May 3, 2016, is named B10007B_SL.txt and is 6,191,728 bytes in size.

FIELD OF THE INVENTION

The application relates to means, which are notably useful for vaccination against bubonic plague and against pneumonic plague, as well as to the biotechnological and medical applications thereof. The means of the application notably comprise Yersinia pseudotuberculosis cells or strains, which express at least one Yersinia pestis Caf1 polypeptide or at least one antigenic fragment of Y. pestis Caf1. More particularly, the means of the application comprise Yersinia pseudotuberculosis cells or strains, which express the Y. pestis F1 protein or capsule.

BACKGROUND OF THE INVENTION

Yersinia pestis, the causative agent of plague, is among the deadliest infectious agents affecting humans. Transmitted by infected fleas, Y. pestis causes primarily bubonic plague. The disease occasionally evolves to pneumonic plague, the most deadly and contagious form of the infection, which is then transmitted from human to human by aerosols.

Since the beginning of the nineties, plague has been included in the list of re-emerging diseases and Y. pestis is classified as a potential biological weapon for terrorist use. Because antibiotic resistant strains of Y. pestis have been observed or could be engineered for evil use, vaccination against plague might become the only means to fight against the disease.

Most efforts made in the recent years focused on subunit formulations combining the capsular F1 antigen and the V antigen (LcrV). Such vaccines however require the use of an adjuvant and repeated injections to confer a mostly antibody-dependent protection.

Other strategies included the attenuation of live Y. pestis by genetic engineering, the introduction of Y. pestis antigens in Salmonella or virus vectors, and DNA vaccination. However, such vaccines are not sufficiently safe and/or efficient against both bubonic plague and pulmonary plague.

Derbise et al. 2012 [bibliographic reference (1)], which has been published on Feb. 14, 2012, describes the construction of a live vaccine against plague. More precisely, it describes the cloning of the Yersinia pestis caf operon, which codes for surface-expression of the oligomeric Y. pestis F1 antigen and insertion of said operon on a plasmid for electroporation into an attenuated strain of Yersinia pseudotuberculosis. In the resulting Y. pseudotuberculosis strain (strain V674pF1), the nucleic acid coding for surface-expression of the monomer unit of the Y. pestis F1 (i.e., at least the Caf1 polypeptide) is contained in said plasmid.

In the Yersinia pseudotuberculosis cells or strains of the application, the nucleic acid coding for surface-expression of the Caf1 polypeptide is contained in the chromosome of said Y. pseudotuberculosis cells or strains. The application demonstrates an exceptionally high vaccination efficacy against both bubonic plague and pneumonic plague. The application further provides comparative experimental data, which notably demonstrate that the cells or strains of the application are more efficient than the V674pF1 strain described in Derbise et al. 2012.

SUMMARY OF THE INVENTION

The present application relates to the subject-matter as defined in the claims as filed and as herein described.

More particularly, the application relates to cell(s), strain(s), composition(s), pharmaceutical composition(s), immunogenic composition(s), vaccine(s), as well as to the biotechnological and medical applications thereof, more particularly to the in vitro and in vivo applications thereof, more particularly to the immunogenic and/or vaccine applications thereof.

A cell of the application is a Yersinia pseudotuberculosis cell, more particularly a recombinant Yersinia pseudotuberculosis cell.

When used for therapeutic purposes, the Yersinia pseudotuberculosis cell of the application is avirulent, more particularly attenuated, still more particularly genetically attenuated.

The Yersinia pseudotuberculosis cell of the application comprises nucleic acid coding for at least one Yersinia pestis Caf1 polypeptide or for at least one antigenic fragment of Yersinia pestis Caf1. More particularly, said nucleic acid codes for the Yersinia pestis F1 protein, still more particularly for the Y. pestis capsule.

Said coding nucleic acid is comprised in, more particularly integrated into the chromosome of the Yersinia pseudotuberculosis cell of the application.

A cell of the application is notably useful as an immunogen against plague, more particularly against both bubonic plague and pulmonary plague.

Chromosomal insertion of said coding nucleic acid leads to unexpectedly higher levels of protection against both bubonic plague and pneumonic plague, more particularly against bubonic plague.

A genetically attenuated Y. pseudotuberculosis cell of the application notably has the following advantages:
  genetic stability: the genome of said Y. pseudotuberculosis cell is much more stable than that of Y. pestis;
  innocuity: said Y. pseudotuberculosis cell can be highly attenuated, e.g., by (partial or complete) deletion of one or more genes essential to virulence mechanism(s), more particularly of three genes essential to distinct virulence mechanisms;
  molecular diversity: when used as a live whole cell vaccine, it offers a high antigenic complexity, which guarantees a response against a broad range of antigenic targets; antigens are in their native form, adequately processed, and produced de novo as long as the bacteria persist;
  easy manufacturing: once developed and validated, live vaccines do not require sophisticated equipments and techniques to be produced;
  immunogenicity: adjuvant is not required, since bacterial antigens (LPS and other pathogen associated signatures) trigger the innate immune system; in addition to antigens common to Y. pestis and Y. pseudotuberculosis, said Y. pseudotuberculosis cell can stably produce the Y. pestis F1 capsule, which is a major vaccine target against Y. pestis;
  single dose administration: this is a major advantage as it greatly facilitates vaccination campaigns and allows a rapid protection;

vaccination possible by two routes: depending on the context, a subcutaneous or oral route of vaccination may be preferred.

The inventors consider that the level of protection against bubonic plague and pneumonic plague that is achieved by the means of the application is one of the most, and probably the most efficient ever reported.

BRIEF DESCRIPTION OF THE FIGURES

Squares=attenuated *Y. pseudotuberculosis* cells, wherein the *Y. pestis* caf operon is carried on a plasmid (*Y. pseudotuberculosis* strain V674pF1).

Triangles=attenuated *Y. pseudotuberculosis* cells, wherein the *Y. pestis* caf operon is inserted into the chromosome (*Y. pseudotuberculosis* strain V674TnF1).

DETAILED DESCRIPTION OF THE INVENTION

The application relates to a *Yersinia pseudotuberculosis* cell.

Said *Yersinia pseudotuberculosis* cell is a recombinant cell.

Said *Y. pseudotuberculosis* cell can be of any serotype, e.g., of serotype I, II, III, IV or V, for example of serotype I. Said *Y. pseudotuberculosis* cell can be a cell of any *Y. pseudotuberculosis* strain.

According to an embodiment of the application, said *Y. pseudotuberculosis* cell or strain is of serotype I.

*Y. pseudotuberculosis* strains are available to the person of ordinary skill in the art, e.g., from collections of microorganisms (e.g., CRBIP, DSMZ, ATCC, NCTC), from commercial sources or by isolation from contaminated biological material (e.g., from contaminated water or soil) or from a contaminated organism (e.g., an infected human or an infected non-human animal).

According to an embodiment of the application, said *Y. pseudotuberculosis* cell or strain is *Y. pseudotuberculosis* IP32953 that comes from the collection of the *Yersinia* Research Unit and National Reference Laboratory [the genome sequence of strain IP32953 is available under accession number NC_006155 (SEQ ID NO: 19), more particularly NC_006155.1 (SEQ ID NO: 19)].

*Y. pseudotuberculosis* is en enteric pathogen. *Y. pseudotuberculosis* infection (or *pseudotuberculosis*) leads to acute digestive disease, sometimes followed by septicemia, and sometimes, but rarely articular and/or cutaneous symptoms.

*Y. pseudotuberculosis* infection in humans usually leads to gastroenteritis. In some countries such as Russia and Japan, specific strains of *Y. pseudotuberculosis* cause Far East scarlet-like fever (FESLF), characterized by erythematous skin rash, desquamation, exanthema, hyperhemic tongue, reactive arthritis, toxic shock syndrome, septicemia.

In non-human animals, *Y. pseudotuberculosis* is a frequent cause of morbidity and sometimes mortality.

Therefore, when the *Y. pseudotuberculosis* cell of the application is intended for a therapeutic application, it is (or has been made) avirulent, i.e., said *Y. pseudotuberculosis* cell is safe enough to be administered without any danger of clinical infection, either for the recipient or for any contact of the recipient. In other words, the risk associated with the administration of said *Y. pseudotuberculosis* is minimized, if not totally eliminated.

More particularly, said *Y. pseudotuberculosis* cell has lost the ability to cause *pseudotuberculosis*, more generally to cause enteric disease and septicemia.

According to an embodiment of the application, said avirulent *Y. pseudotuberculosis* cell is still capable of growth, more particularly of replication in a host organism (such as a human or a non-human mammal), but has lost ability to cause said disease in said host organism.

According to an embodiment of the application, said *Y. pseudotuberculosis* cell is avirulent to a healthy mammal, more particularly to a healthy human being.

Said *Y. pseudotuberculosis* cell can be naturally avirulent, or it can be avirulent by genetic and/or chemical attenuation.

Methods for attenuation of pathogenic bacteria are known in the art. Genetic attenuation can be achieved by inactivating one or more gene(s) involved in metabolic pathway(s) of the bacteria, more particularly in one or more pathogenic mechanism(s) of the bacteria, and/or by inactivating one or more gene(s) involved in or responsible for the production of virulence factor(s) of the bacteria.

According to an embodiment of the application, said *Y. pseudotuberculosis* cell is genetically attenuated.

According to an embodiment of the application, said *Y. pseudotuberculosis* cell is irreversibly attenuated.

According to an embodiment of the application, said *Y. pseudotuberculosis* cell is genetically and irreversibly attenuated.

According to an embodiment of the application, said *Y. pseudotuberculosis* cell is attenuated by partial or complete deletion of one or more genes, still more particularly by partial or complete deletion of one or more genes involved in or responsible for the production of virulence factor(s) of *Y. pseudotuberculosis*. Such genes comprise the High Pathogenicity Island genes (HPI), the yopK gene and the psaA gene.

Partial or complete deletion of genes can be achieved e.g., by allelic exchange following homologous recombination (cf. bibliographic references (1) and (8), i.e., Derbise et al. 2012 and 2003).

Partial deletion is achieved to an extent sufficient to inactivate the function of the gene.

According to an embodiment of the application, said *Y. pseudotuberculosis* cell is attenuated by partial or complete deletion of one or more genes selected from the HPI genes, the yopK gene and the psaA gene, for example by partial or complete deletion of two or more genes selected from the HPI genes, the yopK gene and the psaA gene.

According to an embodiment of the application, said *Y. pseudotuberculosis* cell is attenuated:
- by partial or complete deletion of at least one of the yopK and the psaA genes, still more particularly
- by partial or complete deletion of at least one of the HPI genes, still more particularly
- by partial or complete deletion of at least one HPI gene, which is a YPTB gene, still more particularly
- by partial or complete deletion of at least the HPI genes YPTB1585 to YPTB1602 (YPTB genes as identified in the *Y. pseudotuberculosis* strain IP32953, the genome sequence of which is available under NC_006155 (SEQ ID NO: 19), more particularly under NC_006155.1 (SEQ ID NO: 19)), still more particularly
- by partial or complete deletion of a number of HPI genes that is sufficient to attenuate the HPI-induced virulence, still more particularly
- by partial or complete deletion of all the HPI genes, still more particularly
- by partial or complete deletion of at least one of the yopK and the psaA genes and by partial or complete deletion of at least one, at least two or all of the HPI genes, or at least from YPTB1585 to YPTB1602, still more particularly
- by partial or complete deletion of at least one of the yopK and the psaA genes and by partial or complete deletion of at least from YPTB1585 to YPTB1602, still more particularly
- by partial or complete deletion of the yopK and the psaA genes and by partial or complete deletion of at least one, at least two or all of the HPI genes;
- by partial or complete deletion of the yopK and the psaA genes and by partial or complete deletion of at least from YPTB1585 to YPTB1602

According to an embodiment of the application, said *Y. pseudotuberculosis* cell is attenuated by partial or complete deletion of the HPI genes YPTB1585 to YPTB1602, of the yopK gene and of the psaA gene, still more particularly by partial deletion of the HPI genes, of the yopK gene and of the psaA gene.

Illustrative *Y. pseudotuberculosis* HPI gene sequences are available and identified in the genome sequence of *Y. pseudotuberculosis* strain IP32953 (genome sequence NC_006155 (SEQ ID NO: 19), more particularly NC_006155.1 (SEQ ID NO: 19)). For example, the YPTB1585 through YPTB1602 sequences extend from position 1,914,026 to position 1,949,600 of said genome sequence.

An illustrative *Y. pseudotuberculosis* yopK gene sequence is available and identified in the pYV plasmid sequence of *Y. pseudotuberculosis* IP32953 (plasmid sequence NC_006153, more particularly NC_006153.2). For example, the yopK sequence extends from position 28,491 to position 29,039 of said *Y. pseudotuberculosis* plasmid sequence (complement sequence).

An illustrative *Y. pseudotuberculosis* psaA gene sequence is available and identified in the genome sequence of *Y. pseudotuberculosis* strain IP32953 (genome sequence NC_006155 (SEQ ID NO: 19), more particularly NC_006155.1 (SEQ ID NO: 19)). For example, the psaA sequence extends from position 1,588,872 to position 1,589,348 of said genome sequence.

According to an alternative or complementary embodiment of the application, said *Y. pseudotuberculosis* cell is strongly attenuated, e.g., its $LD_{50}$ for mice is higher than $10^{10}$ CFU via the oral route.

Said *Y. pseudotuberculosis* cell can be a killed cell or a live cell.

According to an advantageous embodiment of the application, said *Y. pseudotuberculosis* cell is a live cell. According to an advantageous embodiment of the application, said *Y. pseudotuberculosis* cell has retained the capacity of in vitro and/or in vivo replication, e.g., in vitro replication on a culture medium such as the Luria Bertani Broth (LB) medium and/or in vivo replication in a non-human mammal such as a mouse or in a human.

The *Y. pseudotuberculosis* cell of the application comprises nucleic acid coding for at least one *Yersinia pestis* Caf1 polypeptide or for at least one antigenic fragment of *Y. pestis* Caf1.

More particularly, the *Y. pseudotuberculosis* cell of the application comprises nucleic acid coding for surface-expression of at least one *Yersinia pestis* Caf1 polypeptide or for surface-expression of at least one antigenic fragment of *Y. pestis* Caf1.

*Yersinia pestis* Caf1 is a polypeptide that is expressed by naturally-occurring *Y. pestis* cells.

*Y. pestis* Caf1 is the monomer subunit that forms the major component of the pathogen capsule, i.e., the *Y. pestis* fraction 1 antigen (F1).

*Y. pestis* F1 is known to be involved in *Y. pestis* resistance to phagocytosis.

The naturally-occurring biogenesis process follows a chaperone/usher pathway, according to which *Y. pestis* Caf1 polypeptides are transported from the inner membrane to the outer membrane, and are assembled in oligomeric form at the bacterial surface, whereby forming the F1 protein.

In the periplasm, a chaperone protein (Caf1M) binds to a Caf1 polypeptide and transport it to the outer membrane. The chaperone:Caf1 complexes are then targeted to the usher (Caf1A), located in the outer membrane, where the Caf1 signal peptide is cleaved and where the mature Caf1 polypeptides are joined together to form a growing chain, which is subsequently translocated through the outer membrane to the surface of the bacteria.

The Caf1 monomer has a molecular weight (MW) of about 17.6 kDa before cleavage of the signal peptide.

After cleavage of the signal peptide sequence, the mature Caf1 monomer has a MW of about 15.5-16.5 kDa. The calculated pI is of about 4.3.

The Caf1 oligomer that is formed at the bacterial surface generally has a MW higher than 1,000 kDa.

*Y. pestis* can be classified into at least three biotypes [Antigua (A), Medievalis (M) or Orientalis (O)] on the basis of their ability to use glycerol and to reduce nitrate.

In the application, *Y. pestis* can be of any biotype, e.g., of the A biotype, or of the M biotype or of the O biotype, for example of the M or O biotype, more particularly of the O biotype.

*Y. pestis* strains are available to the person of ordinary skill in the art, e.g., from collections of microorganisms, from commercial sources or by isolation from a contaminated organism (e.g., from an infected human or from an infected non-human animal or mammal or from an infected insect such as an infected flea).

Illustrative *Y. pestis* e.g. comprise:
the CO92 strain (O biotype);
the KIM10+ strain (M biotype);
the *Y. pestis* strain that is available from NCTC under n° NCTC 5923;
the *Y. pestis* strain that is available from NCTC under n° NCTC 2868;
the *Y. pestis* strain that is available from NCTC under n° NCTC 10329;
the *Y. pestis* strain that is available from NCTC under n° NCTC 10330;

Means for cloning the caf1 gene (and/or for cloning the caf operon) from *Y. pestis* cells are known and available to the person of average skill in the art. Such means e.g., comprise those described in the examples below.

An illustrative *Y. pestis* Caf1 sequence is:
the sequence that is available under accession number P26948 (170 amino acids), which comprises the Caf1 signal peptide (first 21 N-terminal amino acids) and the mature Caf1 (amino acids 22-170), i.e., the sequence of SEQ ID NO: 10, which is:

MKKISSVIAIALFGTIATANAADLTASTTATATLVEPARITLTYKEG

APITIMDNGNIDTELLVGTLTLGGYKTGTTSTSVNFTDAAGDPMYLT

FTSQDGNNHQFTTKVIGKDSRDFDISPKVNGENLVGDDVVLATGSQD

FFVRSIGSKGGKLAAGKYTDAVTVTVSNQ;

or
the corresponding mature Caf1 protein sequence, i.e., the sequence of SEQ ID NO: 12, which is SEQ ID NO: 10 deleted from the peptide signal sequence, i.e.:

ADLTASTTATATLVEPARITLTYKEGAPITIMDNGNIDTELLVGTLT

LGGYKTGTTSTSVNFTDAAGDPMYLTFTSQDGNNHQFTTKVIGKDSR

DFDISPKVNGENLVGDDVVLATGSQDFFVRSIGSKGGKLAAGKYTDA

VTVTVSNQ.

An illustrative sequence coding for *Y. pestis* Caf1 is available and identified in the *Y. pestis* caf operon (operon sequence X61996.1). For example, the caf1 sequence extends from position 4618 to position 5130 of said *Y. pestis* caf operon sequence.) i.e., the sequence of SEQ ID NO: 9 (which codes for the sequence of SEQ ID NO: 10), which is:

ATGAAAAAAATCAGTTCCGTTATCGCCATTGCATTATTTGGAACTAT

TGCAACTGCTAATGCGGCAGATTTAACTGCAAGCACCACTGCAACGG

CAACTCTTGTTGAACCAGCCCGCATCACTCTTACATATAAGGAAGGC

GCTCCAATTACAATTATGGACAATGGAAACATCGATACAGAATTACT

TGTTGGTACGCTTACTCTTGGCGGCTATAAAACAGGAACCACTAGCA

CATCTGTTAACTTTACAGATGCCGCGGGTGATCCCATGTACTTAACA

TTTACTTCTCAGGATGGAAATAACCACCAATTCACTACAAAAGTGAT

TGGCAAGGATTCTAGAGATTTTGATATCTCTCCTAAGGTAAACGGTG

AGAACCTTGTGGGGGATGACGTCGTCTTGGCTACGGGCAGCCAGGAT

TTCTTTGTTCGCTCAATTGGTTCCAAAGGCGGTAAACTTGCAGCAGG

TAAATACACTGATGCTGTAACCGTAACCGTATCTAACCAATAA;

or the sequence of SEQ ID NO: 11 (which codes for the sequence of SEQ ID NO: 12), which is the sequence of SEQ ID NO: 9 deleted from the signal peptide sequence, i.e.:

GCAGATTTAACTGCAAGCACCACTGCAACGGCAACTCTTGTTGAACC

AGCCCGCATCACTCTTACATATAAGGAAGGCGCTCCAATTACAATTA

TGGACAATGGAAACATCGATACAGAATTACTTGTTGGTACGCTTACT

CTTGGCGGCTATAAAACAGGAACCACTAGCACATCTGTTAACTTTAC

AGATGCCGCGGGTGATCCCATGTACTTAACATTTACTTCTCAGGATG

GAAATAACCACCAATTCACTACAAAAGTGATTGGCAAGGATTCTAGA

GATTTTGATATCTCTCCTAAGGTAAACGGTGAGAACCTTGTGGGGGA

TGACGTCGTCTTGGCTACGGGCAGCCAGGATTTCTTTGTTCGCTCAA

TTGGTTCCAAAGGCGGTAAACTTGCAGCAGGTAAATACACTGATGCT

GTAACCGTAACCGTATCTAACCAATAA.

Antigenic fragments of said *Y. pestis* Caf1 notably comprise those Caf1 fragments, which have retained the ability to induce or stimulate a cell-mediated immune response in a human or in a non-human mammal, more particularly the ability to induce or stimulate T cells in a human or in a non-human mammal.

Antigenic fragments of said *Y. pestis* Caf1 also comprise those Caf1 fragments, which show said ability when coupled to an immunogenicity carrier, such as keyhole limpet hemocyanin, horseshoe crab hemocyanin, bovine serum albumin.

Said nucleic acid, which codes for at least one *Yersinia pestis* Caf1 polypeptide and its export machinery or for at least one antigenic fragment of *Y. pestis* Caf1, is comprised in (more particularly, has been inserted in or integrated into) the chromosome of said *Y. pseudotuberculosis* cell, more particularly in the chromosomal DNA of said *Y. pseudotuberculosis* cell.

According to an embodiment of the application, said nucleic acid is stably comprised in (more particularly, inserted in or integrated into) said chromosome or chromosomal DNA.

According to an embodiment of the application, said nucleic acid is irreversibly comprised in (more particularly, inserted in or integrated into) said chromosome or chromosomal DNA.

According to an embodiment of the application, said nucleic acid is stably and/or irreversibly comprised in (more particularly, inserted in or integrated into) said chromosome or chromosomal DNA.

Means for inserting or integrating said nucleic acid in the chromosome of said *Y. pseudotubercolisis* cell, more particularly for stably and/or irreversibly inserting or integrating said nucleic acid in the chromosome of said *Y. pseudotubercolisis* cell, are available to the person of ordinary skill in the art.

Illustrative means comprise:
retroviral integration means;
transposon means.

Advantageously, said means are transposon means, more particularly DNA transposon means, more particularly mini-transposon means, still more particularly Tn7 mini-transposon means.

Illustrative transposon means comprise a carrier or delivery plasmid, wherein the nucleic acid to be transposed is inserted between the transposon ends (e.g., between Tn7L and Tn7R, which are the ends of the Tn7 mini-transposon). Illustrative transposon means may further comprise a helper plasmid, which carries transposase genes (e.g., the Tn7 transposes genes tnsABCDE), for insertion of the transposon in the target chromosome.

Figure 1:
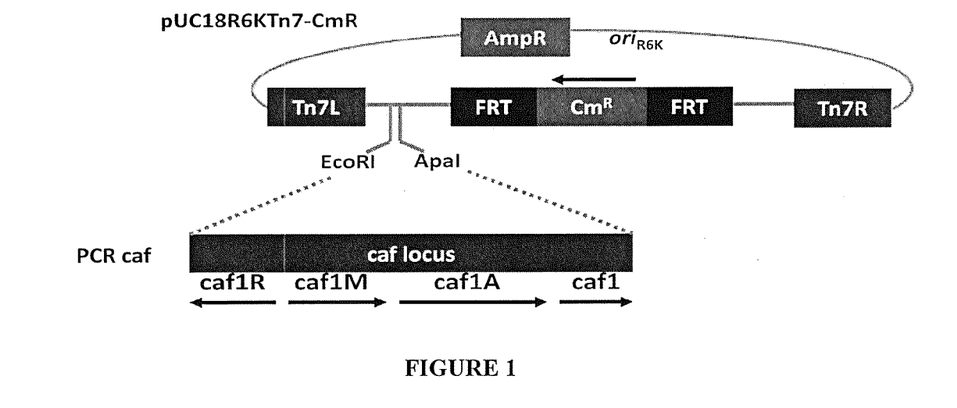
FIG. 1: Genetic map of the recombinant plasmid pUC18R6KTn7-caf-Cm$^R$, which carries the caf operon [caf1M, caf1A and caf1 (under the control of caf1R as regulatory sequence)] inserted in the Tn7 mini-transposon.
Figure 2:
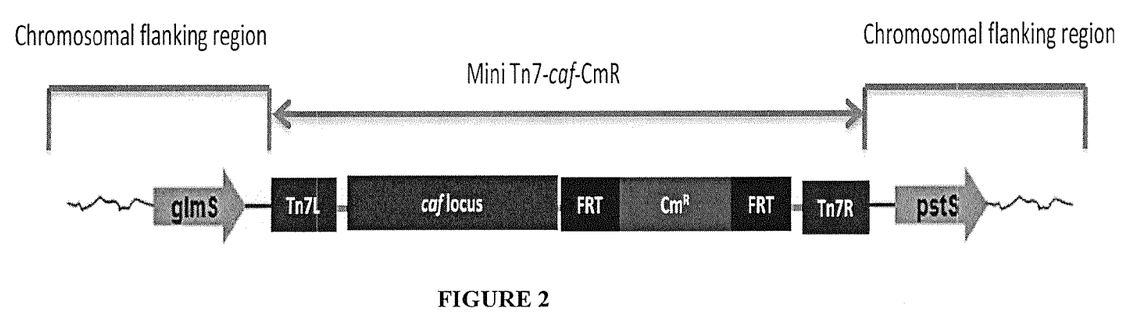
FIG. 2: Genetic map of the mini Tn7-caf-Cm$^R$ transposon integrated into the chromosome of an attenuated *Y. pseudotuberculosis* strain.

Illustrative transposon means are e.g., as described:
in bibliographic reference (2), i.e., Choi et al. 2005, and/or
in the examples below, and/or
in FIG. 1, and/or
in FIG. 2, and/or
in bibliographic reference (10), i.e., Grinter 1983, and/or
in bibliographic reference (11), i.e., Barry et al. 1986, and/or
in bibliographic reference (12), i.e., Bao et al. 1991, and/or
in bibliographic reference (13), i.e., Højberg et al. 1999, and/or
in bibliographic reference (14), i.e., Koch et al. 2001.

According to an advantageous embodiment of the application, said nucleic acid, which codes for at least one *Yersinia pestis* Caf1 polypeptide or for at least one antigenic fragment of *Y. pestis* Caf1, has been inserted in or integrated into the chromosome of said *Y. pseudotuberculosis* cell, more particularly in the chromosomal DNA of said *Y. pseudotuberculosis* cell, by nucleic acid transposition.

According to an advantageous embodiment of the application, at least one transposon carrying the caf operon is integrated in the chromosome of said *Y. pseudotuberculosis* cell.

According to an advantageous embodiment of the application, the chromosome of the *Y. pseudotuberculosis* cell comprises said coding nucleic (e.g., the *Y. pestis* operon encoding the F1 protein or capsule) and two transposon ends (e.g., Tn7L and Tn7R, which are the ends of the Tn7 transposon and of the Tn7 mini-transposon).

The nucleic acid, which codes for said at least one *Y. pestis* Caf1 polypeptide (e.g., the *Y. pestis* operon encoding the F1 protein or capsule) or for said at least one antigenic fragment of *Y. pestis* Caf1, can e.g., be inserted into the chromosome of an attenuated *Y. pseudotuberculosis* strain, e.g., as described above and in the examples and/or figures below.

According to an embodiment of the application, said nucleic acid, which codes for at least one *Y. pestis* Caf1 polypeptide or for at least one antigenic fragment of *Y. pestis* Caf1, is a nucleic acid that codes for expression of said at least one *Y. pestis* Caf1 polypeptide or of said at least one antigenic fragment of *Y. pestis* Caf1 at the surface of said genetically attenuated *Y. pseudotuberculosis* cell.

Said at least one surface-expressed *Y. pestis* Caf1 polypeptide can be contained in an oligomer, more particularly in an oligomer essentially consisting of *Y. pestis* Caf1 monomers.

Advantageously, said oligomer is the *Y. pestis* F1 protein.

Hence, said at least one surface-expressed *Y. pestis* Caf1 polypeptide can e.g., be contained in or expressed in the form of a *Y. pestis* F1 protein.

Said at least one surface-expressed *Y. pestis* Caf1 polypeptide can e.g., be expressed as a component of a capsule surrounding said *Y. pseudotuberculosis* cell.

According to an embodiment of the application, said *Y. pseudotuberculosis* cell expresses or can express the *Y. pestis* F1 protein at its surface.

According to an embodiment of the application, said *Y. pseudotuberculosis* cell expresses or can express the *Y. pestis* capsule, i.e., the *Y. pestis* F1 capsule.

According to an embodiment of the application, said *Y. pseudotuberculosis* cell is encapsulated.

According to an embodiment of the application, said *Y. pseudotuberculosis* cell is surrounded by the *Y. pestis* capsule or by components thereof.

According to an embodiment of the application, said *Y. pseudotuberculosis* cell is recognized (i.e., bound) by an anti-*Y. pestis* F1 monoclonal antibody, more particularly specifically recognized (i.e., bound) by an anti-*Y. pestis* F1 monoclonal antibody (e.g., the monoclonal antibody described in Chanteau et al. 2003 [bibliographic reference 3] or the monoclonal antibody available from QED Bioscience, Inc.; 10919 Technology Place, Suite C; U.S.A.; under catalog n° 18740 (YBF19)).

According to an embodiment of the application, said nucleic acid coding for said at least one *Y. pestis* Caf1 polypeptide or for said at least one antigenic fragment of *Y. pestis* Caf1 (e.g., for at least one *Y. pestis* F1 protein, or for a *Y. pestis* capsule) further comprises one or more gene(s), more particularly one or more structural gene(s):

for expression of said at least one *Y. pestis* Caf1 polypeptide or for said at least one antigenic fragment of *Y. pestis* Caf1 (e.g., for at least one *Y. pestis* F1 protein, or for an *Y. pestis* capsule) in accordance with a chaperone/usher pathway; and/or for surface-expression of said at least one *Y. pestis* Caf1 polypeptide or for said at least one antigenic fragment of *Y. pestis* Caf1 (e.g., for at least one *Y. pestis* F1 protein, or for an *Y. pestis* capsule), more particularly for expression at the surface of said *Y. pseudotuberculosis* cell.

Such further gene(s) can e.g., be:
at least one gene coding for a protein that can act as a chaperone for said at least one *Y. pestis* Caf1 or antigenic Caf1 fragment, such as the *Y. pestis* Caf1M, and/or, more particularly and
at least of gene coding for a protein that can act as a usher for said at least one *Y. pestis* Caf1 or antigenic Caf1 fragment, such as the *Y. pestis* Caf1A.

Alternatively or complementarily, said nucleic acid coding for said at least one *Y. pestis* Caf1 polypeptide or for said at least one antigenic fragment of *Y. pestis* Caf1 (e.g., for at least one *Y. pestis* F1 protein, or for an *Y. pestis* capsule) further comprises at least one regulatory sequence, such as the *Y. pestis* caf1R regulatory sequence, which controls the expression of at least one *Y. pestis* Caf1 polypeptide or for said at least one antigenic fragment of *Y. pestis* Caf1 (e.g., for at least one *Y. pestis* F1 protein, or for an *Y. pestis* capsule) and/or the expression of said further gene(s).

According to an embodiment of the application, said nucleic acid coding for said at least one *Y. pestis* Caf1 polypeptide or for said at least one antigenic fragment of *Y. pestis* Caf1 (e.g., for at least one *Y. pestis* F1 protein, or for an *Y. pestis* capsule) is an operon.

Said operon advantageously comprises said further gene(s) and/or said at least one regulatory sequence, more particularly said further gene(s) and said at least one regulatory sequence.

Said operon may e.g., comprise at least one gene coding for (at least one) *Y. pestis* Caf1 or at least one antigenic Caf1 fragment, more particularly for (at least one) *Y. pestis* Caf1, and:
- at least one gene coding for a protein that can act as a chaperone for said *Y. pestis* Caf1, such as the *Y. pestis* Caf1M, and/or, more particularly and
- at least of gene coding for a protein that can act as a usher for said *Y. pestis* Caf1, such as the *Y. pestis* Caf1A.

For example, said operon advantageously comprises at least one gene coding for *Y. pestis* Caf1, at least one gene coding for the *Y. pestis* Caf1M chaperone protein and at least one gene coding for the *Y. pestis* Caf1A usher protein.

Said operon may further comprise a regulatory sequence, such as the *Y. pestis* caf1R regulatory sequence, to control the expression of said gene(s).

An illustrative operon is contained in the pMT1 plasmid (accession number AL117211; 96,210 bp) from *Y. pestis* strain CO92, which (inter alia) encodes the *Y. pestis* F1 protein.

An illustrative *Y. pestis* Caf1M protein sequence is the sequence under accession number P26926 (258 amino acids), i.e., the sequence of SEQ ID NO: 14, which is:

MILNRLSTLGIITFGMLSFAANSAQPDIKFASKEYGVTIGESRIIYP

LDAAGVMVSVKNTQDYPVLIQSRIYDENKEKESEDPFVVTPPLFRLD

AKQQNSLRIAQAGGVFPRDKESLKWLCVKGIPPKDEDIWVDDATNKQ

KFNPDKDVGVFVQFAINNCIKLLVRPNELKGTPIQFAEKLSWKVDGG

KLIAENPSPFYMNIGELTFGGKSIPSHYIPPKSTWAFDLPKGLAGAR

NVSWRIINDQGGLDRLYSKNVTL.

An illustrative sequence coding for an *Y. pestis* Caf1M protein is the sequence of SEQ ID NO: 13 [CDS (AL117211.1:82567 . . . 83343)], which is:

ATGATTTTAAATAGATTAAGTACGTTAGGAATTATTACTTTCGGCAT

GCTTAGTTTTGCTGCGAACTCTGCTCAACCAGATATCAAATTCGCAA

GCAAAGAGTATGGCGTGACTATAGGTGAGAGTAGGATCATATACCCG

TTAGATGCTGCTGGCGTTATGGTCTCGGTGAAAAACACCCAAGATTA

TCCGGTTCTCATTCAGTCTAGGATCTACGACGAGAATAAAGAAAAAG

AATCAGAGGATCCTTTCGTGGTCACTCCGCCATTGTTTCGATTGGAT

GCTAAGCAACAAAATTCTTTGCGTATAGCTCAGGCTGGAGGTGTTTT

CCCGCGAGATAAAGAGAGCCTAAAGTGGTTATGCGTAAAAGGGATTC

CACCAAAGGATGAAGATATATGGGTTGATGATGCGACAAATAAGCAA

AAATTCAATCCAGACAAAGATGTGGGAGTGTTCGTGCAATTCGCAAT

TAATAATTGCATTAAGCTTTTGGTTCGACCGAATGAATTAAAAGGAA

CCCCTATACAGTTTGCTGAAAACTTAAGCTGGAAAGTTGATGGGGGG

AAGCTAATTGCTGAAAACCCCTCACCTTTCTACATGAACATAGGTGA

ATTAACATTTGGAGGGAAAAGTATTCCTTCTCACTATATTCCACCTA

AATCGACGTGGGCTTTTGATTTGCCAAAAGGACTAGCGGGAGCACGT

AATGTTTCGTGGAGAATAATTAATGATCAGGGAGGGTTGGATCGTTT

GTATTCCAAAAATGTGACTTTATGA.

An illustrative *Y. pestis* Caf1A protein sequence is the sequence under accession number P26949 (833 amino acids), i.e., the sequence of SEQ ID NO: 16, which is:

MRYSKLFLCAGLTLATLPCWGRAYTFDSTMLDTNSGESIDVSLFNQG

LQLPGNYFVNVFVNGRKVDSGNIDFRLEKHNGKELLWPCLSSLQLTK

YGIDIDKYPDLIKSGTEQCVDLLAIPHSDVQFYFNQQKLSLIVPPQA

LLPRFDGIMPMQLWDDGIPALFMNYNTNMQTRKFREGGKSLDSYYAQ

LQPGLNIGAWRFRSSTSWWKQQGWQRSYIYAERGLNTIKSRLTLGET

YSDSSIFDSIPIKGIKIASDESMVPYYQWNFAPVVRGIARTQARVEV

LRDGYTVSNELVPSGPFELANLPLGGGSGELKVIIHESDGTKQVFTV

PYDTPAVALRKGYFEYSMMGGEYRPANDLTQTSYVGVFGMKYGLPRN

FTLYGGLQGSQNYHAEALGIGAMLGDFGAISTDVTQADSQKNKQKKE

SGQRWRVRYNKYLQSGTSLNIASEEYATEGFNKLADTLNTYCKPNTR

NDCRFDYAKPKNKVQFNLSQSIPGSGTLNFSGYRKNYWRDSRSTTSF

SVGYNHFFRNGMSLTLNLSKTQNINKYGEKTSELLSNIWLSFPLSRW

LGNNSINSNYQMTSDSHGNTTHEVGVYGEAFDRQLYWDVRERFNEKG

RKYTSNALNLNYRGTYGEISGNYSYDQTQSQLGIGVNGNMVITQYGI

TAGQKTGDTIALVQAPDISGASVGYWPGMKTDFRGYTNYGYLTPYRE

YKVEINPVTLPNDAEITNNIVSVIPTKGAVVLAKFNARIGGRLFLHL

KRSDNKPVPFGSIVTIEGQSSSSGIVGDNSGVYLTGLPKKSKILVKW

GRDKNQSCSSNVVLPEKTDISGAYRLSTTCILNN.

An illustrative sequence coding for an *Y. pestis* Caf1A protein is the sequence of SEQ ID NO: 15 [CDS (AL117211.1:83368 . . . 85869)], which is:

ATGAGGTATTCAAAGCTGTTCCTGTGTGCAGGGTTAACTTTGGCAAC

ATTGCCTTGTTGGGGACGCGCATATACTTTTGACTCTACTATGCTTG

ATACGAATAGTGGAGAGATATAGATGTATCTCTTTTTAATCAAGGA

CTTCAACTTCCAGGTAATTATTTTGTTAATGTTTTTGTAAATGGTCG

AAAGGTAGACTCTGGAAATATCGACTTCCGTCTAGAAAAACATAATG

GAAAAGAACTTCTTTGGCCATGCCTATCATCCTTACAATTGACAAAG

TATGGCATTGATATAGATAAATATCCTGATTTAATAAAATCTGGTAC

AGAGCAATGTGTTGATTTATTAGCAATACCACATTCAGATGTGCAGT

TTTATTTTAATCAGCAGAAATTATCGTTAATTGTGCCACCACAGGCA

-continued
CTTTTACCTAGATTTGATGGCATTATGCCAATGCAATTGTGGGATGA

CGGCATTCCTGCTCTGTTCATGAATTATAATACGAACATGCAGACAA

GAAAATTCAGAGAAGGAGGCAAGTCTCTGGACTCTTATTATGCTCAG

TTGCAACCGGGATTAAACATAGGGGCTTGGCGCTTTCGTAGTTCAAC

CTCATGGTGGAAACAACAAGGATGGCAGCGTTCGTATATTTATGCCG

AGCGAGGATTGAATACAATTAAGAGCCGTTTGACATTGGGGGAAACC

TATTCTGATAGCAGTATCTTTGACAGTATCCCGATTAAGGGGATAAA

AATTGCTTCAGATGAATCGATGGTTCCTTATTACCAATGGAATTTTG

CTCCAGTTGTTCGCGGTATCGCACGTACACAAGCCAGGGTAGAGGTT

TTAAGAGATGGCTACACTGTAAGTAATGAGTTGGTGCCCTCGGGACC

ATTTGAGTTAGCAAATCTTCCTCTGGGTGGGGGGAGTGGTGAGCTGA

AAGTCATCATTCATGAAAGTGATGGAACAAAGCAAGTTTTTACAGTT

CCATATGACACACCAGCAGTGGCATTACGGAAGGGCTATTTCGAATA

TTCAATGATGGGGGGAGAATATCGTCCAGCTAATGATCTTACACAAA

CATCGTATGTTGGCGCTCTTGGGATGAAATATGGTTTGCCAAGGAAT

CTTACGTTATATGGTGGACTACAAGGGTCCCAAAATTATCATGCCGC

AGCTCTGGGTATCGGTGCTATGTTGGGTGATTTTGGTGCCATATCTA

CAGATGTTACTCAAGCAGACAGCCAGAAAATAAACAAAAAAAGAA

AGCGGCCAACGTTGGCGCGTTCGTATATAAGTACTTGCAGAGTGG

AACATCGTTAAACATTGCTAGCGAGGAATACGCCACAGAAGGATTTA

ACAAACTCGCTGACACGTTAAATACTTATTGTAAACCTAATACTAGA

AACGATTGCCGTTTTGATTATGCTAAACCCAAAACAAAGTGCAATT

CAATTTAAGTCAAAGCATACCTGGTTCGGGGACGCTTAATTTCAGTG

GCTACAGAAAAAACTATTGGCGTGACAGTAGGAGCACAACTTCTTTT

TCTGTAGGCTATAACCATTTTTTTAGGAATGGTATGTCATTGACTTT

AAATTTATCGAAGACACAGAATATCAATAAGTATGGAGAAAAAACTA

GTGAGCTATTATCTAATATCTGGTTGAGTTTTCCTCTCAGTCGCTGG

CTAGGTAATAACTCAATAAATTCAAATTACCAAATGACATCAGATTC

TCATGGTAACACTACCCATGAGGTAGGTGTGTACGGTGAAGCCTTTG

ATCGCCAATTATACTGGGACGTTCGCGAACGTTTTAATGAAAAGGGC

AGAAAATATACCTCCAATGCACTGAATTTGAATTATCGAGGAACTTA

TGGGGAGATCAGTGGTAACTACAGCTACGATCAAACCCAAAGCCAAC

TTGGTATAGGTGTAAATGGCAATATGGTAATAACTCAGTACGGTATA

ACGGCTGGCCAAAAAACTGGAGATACTATTGCATTAGTACAAGCCCC

TGATATAAGCGGTGCTTCAGTGGGATACTGGCCAGGCATGAAAACAG

ACTTTAGGGGGTACACCAATTATGGTTACTTAACCCCTTACAGAGAG

AATAAGGTAGAAATTAACCCAGTTACTTTACCCAATGATGCAGAGAT

AACAAATAATATTGTTAGCGTGATCCCGACAAAGGGAGCTGTAGTAT

TAGCAAAATTTAACGCAAGGATTGGTGGACGATTGTTTTTACATTTA

AAACGCTCTGACAATAAACCTGTTCCATTTGGTTCTATAGTTACCAT

TGAAGGGCAATCATCCAGCTCTGGCATTGTCGGAGATAATAGCGGTG

-continued
TCTATTTGACTGGACTACCTAAAAAATCAAAAATACTTGTTAAGTGG

GGGAGAGATAAAAATCAATCATGTTCATCTAATGTAGTTCTACCAGA

AAAAACGGATATTTCTGGTGCTTATAGGTTATCCACAACCTGCATCT

TAAATAACTGA.

An illustrative Y. pestis Caf1R protein sequence is the sequence under accession number P26950 (301 amino acids), i.e., the sequence of SEQ ID NO: 18, which is:

MLKQMTVNSIIQYIEENLESKFINIDCLVLYSGFSRRYLQISFKEYV

GMPIGTYIRVRRASRAAALLRLTRLTHEISAKLFYDSQQTFTREFKK

IFGYTPRQYRMIPFWSFKGLLGRREINCEYLQPRICYLKERNIIGQC

FNFRDLVFYSGIDSKCRLGKLYDSLKKNTAITVSNRIPFHDKTNDII

ARTVVWDRNKHFSDSEIKVDKGLYAYFFFNDTYDQYVHHMYNIYYNS

LPIYNLNKRDGYDVEVIKRRNDNTIDCHYFLPIYCDDMEFYNEMQVY

HNNIVKPEMSVTLGLPKS.

An illustrative sequence coding for an Y. pestis Caf1R protein is the sequence of SEQ ID NO: 17 [complement (AL117211.1:81352 ... 82257)], which is:

ATGCTAAAACAGATGACTGTAAATTCAATTATTCAATATATAGAAGA

GAATCTCGAGTCGAAATTCATTAACATTGACTGTTTGGTTTTGTATT

CAGGATTCAGCAGAAGGTATTTGCAAATTTCCTTTAAGGAATATGTC

GGAATGCCTATTGGAACATATATTAGAGTTAGAAGGGCTAGTAGAGC

TGCTGCACTATTACGGCTTACCAGGCTGACAATAATAGAGATATCAG

CAAAGCTTTTTTATGATTCGCAACAGACATTCACCAGAGAATTTAAG

AAAATATTTGGTTATACCCCACGGCAGTATAGGATGATCCCTTTTTG

GTCCTTTAAAGGTTTGTTGGGTAGAAGGGAAATTAACTGTGAATACC

TTCAACCACGAATCTGTTACCTTAAAGAGAGAAATATAATTGGTCAA

TGCTTTAATTTTAGGGATTTAGTGTTCTACTCTGGGATAGATTCAAA

ATGTAGATTGGGTAAGTTATATGATTCGTTGAAGAAAAATACAGCTA

TAACAGTATCAAACAGAATCCCCTTTCATGATAAAACGAATGACATT

ATTGCAAGAACGGTTGTTTGGGATAGGAATAAGCATTTCAGCGATAG

TGAAATAAAGGTAGATAAAGGCCTGTATGCTTATTTTTTCTTCAATG

ATACATATGATCAGTATGTTCATCACATGTACAACATATATTATAAC

TCTTTGCCTATTTATAATTTAAATAAGCGGGATGGTTACGATGTGGA

GGTCATAAAAAGACGAAATGACAATACTATTGATTGTCATTATTTTC

TCCCGATTTATTGTGATGACATGGAGTTTTACAATGAAATGCAGGTA

TATCACAATAATATTGTGAAGCCGGAAATGTCAGTAACATTAGGATT

ACCAAAGAGTTAA.

According to an embodiment, said nucleic acid comprises at least one gene coding for (at least one) Y. pestis Caf1 or at least one antigenic Caf1 fragment, more particularly for (at least one) Y. pestis Caf1, and (e.g., organized in an operon):

at least one gene coding for the *Y. pestis* Caf1M protein of SEQ ID NO: 14, e.g., the *Y. pestis* caf1M nucleic acid of SEQ ID NO: 13, and/or, more particularly and at least of gene coding for the *Y. pestis* Caf1A protein of SEQ ID NO: 16, e.g., the *Y. pestis* caf1A nucleic acid of SEQ ID NO: 15.

According to an embodiment, said nucleic acid comprises at least one gene coding for (at least one) *Y. pestis* Caf1 or at least one antigenic Caf1 fragment, more particularly for (at least one) *Y. pestis* Caf1, and (e.g., organized in an operon):

at least one gene coding for the *Y. pestis* Caf1M protein of SEQ ID NO: 14, e.g., the *Y. pestis* caf1M nucleic acid of SEQ ID NO: 13, and/or, more particularly and at least of gene coding for the *Y. pestis* Caf1A protein of SEQ ID NO: 16, e.g., the *Y. pestis* caf1A nucleic acid of SEQ ID NO: 15, and/or, more particularly and at least of gene coding for the *Y. pestis* Caf1R protein of SEQ ID NO: 18, e.g., the *Y. pestis* caf1R nucleic acid of SEQ ID NO: 17.

According to an embodiment, the application relates to an avirulent *Yersinia pseudotuberculosis* cell, more particularly to a genetically attenuated *Yersinia pseudotuberculosis* cell, which derives from a *Y. pseudotuberculosis* cell, more particularly from a cell of *Y. pseudotuberculosis* strain IP32953 (the chromosomal sequence of which is the sequence available under accession number NC_006155 (SEQ ID NO: 19)), by:

deletion or inactivation of one or more genes selected from HPI, yopK and psaA (as above described and/or below illustrated) and by chromosomal insertion of said nucleic acid coding for the expression of at least one *Yersinia pestis* Caf1 polypeptide or antigenic fragment at the surface of said *Y. pseudotuberculosis* cell (as above described and/or below illustrated).

The application also relates to a plurality of cells, which comprises at least one *Yersinia pseudotuberculosis* cell of the application, as well as to a *Yersinia pseudotuberculosis* strain, which comprises at least one cell of the application, or which consists or essentially consists of cells of the application.

The application also relates to said *Yersinia pseudotuberculosis* strain, wherein more than 50%, more particularly more than 55%, still more particularly more than 60%, still of more particularly more than 65%, still of more particularly more than 70%, still of more particularly more than 75%, still of more particularly more than 80%, still of more particularly more than 85%, still of more particularly more than 90%, still of more particularly more than 95% of the cells of said strain are encapsulated by a *Y. pestis* pseudo capsule.

Said *Y. pseudotuberculosis* strain advantageously is an avirulent *Y. pseudotubercolis* strain as herein described and/or illustrated. Said *Y. pseudotuberculosis* strain may consist or essentially consist of cells of the application.

The application also relates to said cell, said plurality of cells and to said strains, for use as an immunogen, more particularly for use as an immunogen against plague, still more particularly against bulbonic plague and/or pulmonary plague, still more particularly against bulbonic plague or pulmonary plague, still more particularly against bulbonic plague and pulmonary plague.

In the application, said nucleic acid or operon, which codes for said at least one *Y. pestis* Caf1 polypeptide (e.g., for the *Y. pestis* F1 protein or capsule) or for said at least one antigenic fragment of *Y. pestis* Caf1, more particularly said nucleic acid or operon, which codes for surface expression thereof, is inserted in (or integrated into) the chromosome of *Y. pseudotuberculosis*.

Chromosomal insertion of said nucleic acid or operon leads to unexpectedly higher levels of protection against both bubonic plague and pneumonic plague, more particularly against bubonic plague.

For example, a single oral inoculation of live, attenuated *Y. pseudotuberculosis*, in which the *Y. pestis* F1 operon has been inserted into the chromosome, can achieve:

100% protection against pneumonic plague after a challenge with $3,300 \times LD_{50}$ of *Y. pestis*, as well as 100% protection against bubonic plague after a challenge with $100 \times LD_{50}$ of *Y. pestis* [$LD_{50}$=50% lethal dose].

By comparison, when the *Y. pestis* F1 operon has not been inserted into the chromosome of *Y. pseudotuberculosis*, but is provided by a plasmid contained in *Y. pseudotuberculosis*, the vaccination protection is, under the same experimental conditions, of:

80% against pneumonic plague after a challenge with $3,300 \times LD_{50}$ of *Y. pestis*, and 81% against bubonic plague after a challenge with $100 \times LD_{50}$ of *Y. pestis*.

It is believed that the level of protection against bubonic plague and pneumonic plague that is achieved by the means of the application is one of the most, and probably the most efficient ever reported.

A cell of the application can be used with or without immunologic adjuvant, more particularly with an adjuvant, which accelerates, prolongs, or enhances the quality of immune responses to the *Y. pestis* polypeptide(s) or protein(s) that are expressed at the surface of the *Y. pseudotuberculosis* cell of the application.

Immunologic adjuvants are known to the person of ordinary skill in the art. Illustrative immunologic adjuvant comprises Freund's complete adjuvant, Freund's incomplete adjuvant, the Ribi adjuvant system, an adjuvant based on aluminium salts (e.g., alum) and/or liposomes, bacterial LPS.

Advantageously, a cell of the application can be used without immunologic adjuvant.

Said cell, said plurality of cells or said strain can be administered via any route that the person of ordinary skill in the art may find appropriate.

According to an embodiment of the application, said administration route is a non-invasive route, more particularly a route that does not require the use of any canula or other highly invasive instrument.

According to an embodiment of the application, said administration route is the oral route, the intranasal route, the subcutaneous route, the intradermal route, the intramuscular route.

According to an embodiment of the application, said administration route is a non-oral route, more particularly the intranasal route, the subcutaneous route, the intradermal route, the intramuscular route, more particularly the subcutaneous route.

According to an embodiment of the application, said cell, plurality of cells or strain is administered by spray (e.g., nasal and/or oral spray) and/or by injection (e.g., subcutaneous and/or intramuscular injection), more particularly by injection (e.g., subcutaneous and/or intramuscular injection), more particularly by subcutaneous injection.

Moreover, chromosomal insertion of said nucleic acid or operon may lead to particularly high vaccination efficacy, when the vaccination cells or strain is administered via routes other than the oral route, more particularly via a subcutaneous administration. Via such non-oral, lower doses are required to achieve the same vaccination efficacy and/or the same dose achieves protection against higher *Y. pestis* doses.

Said cell, said plurality of cells or said strain can be administered at any dose that the person of ordinary skill in the art may find appropriate, taking due account of the administration route contemplated and taking due account of the age, weight and health status of the intended recipient.

According to an embodiment of the application, said cell, plurality of cells or strain is administered at a dose sufficient to induce an immune response in the recipient organism, more particularly in a human or non-human animal or non-human mammal.

Said immune response can e.g., comprise a humoral response and/or a cell-mediated immune response, advantageously both a humoral response and a cell-mediated immune response.

According to an embodiment of the application, the dose at which said cell, plurality of cells or strain is administered is sufficient to induce both an immune response and a cell-mediated immune response at both the systemic level (e.g., IgG and Th1 cells) and the mucosal level (e.g., IgA and Th17 cells).

The application also relates to a composition, more particularly a pharmaceutical composition, still more particularly an immunogenic composition or vaccine, which comprises at least one of the following elements:
 at least one cell of the application,
 at least one plurality of cells of the application,
 at least one *Y. pseudotuberculosis* strain of the application.

According to an embodiment of the application, said composition, pharmaceutical composition, immunogenic composition or vaccine is a spray, a vial or a prefilled syringe, more particularly a vial or a prefilled syringe, more particularly a vial, more particularly a sealed vial suitable for storing an injectable product and for aseptically transferring said product from said vial into a syringe (e.g., a vial sealed by a septum or by a septum and a cap).

Said composition, more particularly a pharmaceutical composition, still more particularly an immunogenic composition or vaccine, may further comprise at least one pharmaceutically and/or physiologically acceptable vehicle (diluent, excipient, additive, pH adjuster, emulsifier or dispersing agent, preservative, surfactant, gelling agent, as well as buffering and other stabilizing and solubilizing agent, etc.), more particularly at least one vehicle suitable for vaccine administration to human or non-human animal or non-human mammal.

Appropriate pharmaceutically acceptable vehicles and formulations include all known pharmaceutically acceptable vehicles and formulations, such as those described in "Remington: The Science and Practice of Pharmacy", 20$^{th}$ edition, Mack Publishing Co.; and "Pharmaceutical Dosage Forms and Drug Delivery Systems", Ansel, Popovich and Allen Jr., Lippincott Williams and Wilkins.

In general, the nature of the vehicle will depend on the particular mode of administration being employed. For instance, parenteral formulations usually comprise, injectable fluids that include pharmaceutically and physiologically acceptable fluids, including water, physiological saline, balanced salt solutions, buffers, aqueous dextrose, glycerol, ethanol, sesame oil, combinations thereof, or the like as a vehicle. The medium also may contain conventional pharmaceutical adjunct materials such as, for example, pharmaceutically acceptable salts to adjust the osmotic pressure, buffers, preservatives and the like. The carrier and composition can be sterile, and the formulation suits the mode of administration.

A composition, pharmaceutical composition, immunogenic composition or vaccine of the application can e.g., be a liquid solution, suspension, emulsion, sustained release formulation, or powder.

Said composition, more particularly said pharmaceutical composition, still more particularly said immunogenic composition or vaccine, may further comprise an immunologic adjuvant, e.g., as above-described. However, an advantageous feature of the cell, plurality of cells and strain of the application is that such an adjuvant is not necessarily needed for induction of a protective effect.

The application also relates to a method of treatment of a subject in need thereof, e.g., a human, a non-human animal or a non-human mammal, which comprises administering to said subject at least one cell, plurality of cells or strain of the application, more particularly at a dose sufficient to induce an immune response as above-described.

The application relates to a method for preventing or treating *Y. pestis* infection in a mammal, which comprises administering to said mammal at least one avirulent *Yersinia pseudotuberculosis* cell, plurality of cells or strain of the application, more particularly at least one genetically attenuated *Yersinia pseudotuberculosis* cell, plurality of cells or strain of the application. Said at least one avirulent or genetically attenuated *Yersinia pseudotuberculosis* cell, plurality of cells or strain of the application can be administered to said mammal at a dose sufficient to induce an immune response as above-described, more particularly at a single unit dose. Said mammal can be a human or a non-human mammal, more particularly a human.

The application also relates to a method of administering an anti-plague immunogenic composition or vaccine, which comprises administering at least one cell, plurality of cells or strain of the application, or at least one composition, pharmaceutical composition, immunogenic composition or vaccine.

The cell, plurality of cells, strain(s), composition(s), pharmaceutical composition(s), immunogenic composition(s), vaccine(s) of the application are more particularly intended for administration to:
 a human, which is at risk to be in contact with or exposed to *Y. pestis*, more particularly to laboratory researchers, doctors, health therapists, people working in or for medical analysis laboratory, people working in or for the army or in a military environment;
 to a non-human animal, more particularly to a non-human mammal, more particularly a rodent, still more particularly to a rat or a mouse.

The application also relates to the use, more particularly to the in vitro use of a *Y. pseudotuberculosis* cell as a host cell for expression of at least one *Y. pestis* Caf1 polypeptide or of at least one antigenic fragment of *Y. pestis* Caf1, wherein nucleic acid coding for said at least one *Y. pestis* Caf1 polypeptide is comprised in the chromosome of said *Y. pseudotuberculosis* cell.

In the present application, CNCM means Collection Nationale de Cultures de Micro-organismes. The address of CNCM is: Collection Nationale de Cultures de Micro-organismes (CNCM); Institut Pasteur; 28, rue du Dr Roux; 75724 Paris Cedex 15; France.

In the present application, CRBIP means Biological Resource Center of Institut Pasteur. The address of CRBIP is: Institut Pasteur; Centre de Ressources Biologiques; 25-28 rue du Docteur Roux; 75015 Paris; France.

In the present application, NCTC means National Collection of Type Cultures. The address of NCTC is: Health Protection Agency Culture Collections; Health Protection Agency; Microbiology Services; Porton Down; Salisbury; SP4 OJG; United Kingdom.

In the present application, DSMZ means Deutsche Sammlung von Mikroorganismen and Zellkulturen GmbH. The address of DSMZ is: Leibniz Institute DSMZ—German Collection of Microorganisms and Cell Cultures; Inhoffenstr. 7B; D-38124 Braunschweig; Germany.

In the present application, ATCC means American Type Culture Collection. The address of ATCC is: American Type Culture Collection (ATCC); 10801 University Blvd.; Manassas, Va. 20110-2209; United States of America.

In the application, unless specified otherwise or unless a context dictates otherwise, all the terms have their ordinary meaning in the relevant field(s).

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

In an attempt to help the reader of the present application, the description has been separated in various paragraphs or sections and/or in various embodiments. These separations should not be considered as disconnecting the substance of a paragraph or section and/or of an embodiment from the substance of another paragraph or section and/or of another embodiment. To the contrary, the present application encompasses all the combinations of the various sections, paragraphs and sentences that can be contemplated. The present application encompasses all the combinations of the various embodiments that are herein described.

Each of the relevant disclosures of all references cited herein is specifically incorporated by reference. The following examples are offered by way of illustration, and not by way of limitation.

EXAMPLES

Example 1

We produced a *Y. pseudotuberculosis* strain, which is both avirulent and genetically defined for use as vaccine against plague. To this end, we irreversibly attenuated the *Y. pseudotuberculosis* IP32953 strain by deletion of genes encoding three essential virulence factors (the High pathogenicity island, YopK and the pH6 Ag/PsaA).

We cloned the *Y. pestis* F1-encoding caf operon in a plasmid and introduced it into the attenuated *Y. pseudotuberculosis* strain, whereby generating an encapsulated derivative of attenuated *Y. pseudotuberculosis* strain. The resulting strain, named V674pF1 (1), produced the F1 capsule in vitro and in vivo. Oral inoculation of V674pF1 allowed the colonization of the gut without causing lesions in Peyer's patches and the spleen. Vaccination with V674pF1 induced both humoral and cellular components of immunity, at the systemic (IgG and Th1 cells) and the mucosal levels (IgA and Th17 cells). A single oral dose ($10^8$ CFU) protected 100% of animals against pneumonic plague (challenge dose $10^5$ CFU, i.e., 33×$LD_{50}$) and 94% with a higher dose ($10^3$ CFU, i.e., 3,300×$LD_{50}$) (1).

However, this vaccination protocol protected only 81% of the animals against bubonic plague with a low challenge dose ($10^3$ CFU, i.e., 100×$LD_{50}$) (cf. results below and FIG. 7A). In addition, we observed that production of the F1 capsule was unstable.

We generated another form of encapsulated derivative by inserting the *Y. pestis* caf operon encoding F1 into the chromosome of the attenuated *Y. pseudotuberculosis* strain, using a Tn7 mini-transposon. The resulting strain, named V674TnF1, was compared to strain V674pF1 for stability of F1 production, potential residual virulence of the strain and protective efficacy.

Ethics

Animals were housed in the Institut Pasteur animal facilities accredited by the French Ministry of Agriculture to perform experiments on live mice (accreditation B 75 15-01, issued on May 22, 2008), in appliance of the French and European regulations on care on protection of the Laboratory Animals (ED Directive 86/609, French Law 2001-486 issued on Jun. 6, 2001). Protocols were approved by the veterinary staff of the Institut Pasteur animal facility and were performed in compliance with the NIH Animal Welfare Insurance #A5476-01 issued on Feb. 7, 2007.

*Y. pestis* Strain

*Y. pestis* strain CO92 is a wild type strain of the Orientalis biotype (5).

The complete genome sequence of *Y. pestis* strain CO92 is available under accession number AL590842. In addition, *Y. pestis* strain CO92 contains three plasmids: pMT1 (also named pFra; accession number AL117211), pCD1 (also named pYV; accession number AL117189), and pPCP1 (also named pPLa; accession number AL109969). Plasmid pMT1 contains the caf operon and encodes the F1 capsule.

*Y. pseudotuberculosis* Strains

The *Y. pseudotuberculosis* IP32953 strain is a wild type serotype I strain (6). The complete genome sequence of *Y. pseudotuberculosis* IP32953 is available from NCBI under NC_006155 (SEQ ID NO: 19).

Strain IP32953p was produced by introduction of plasmid pKOBEG-sacB into strain IP32953 by electroporation (7). The vector pKOBEG-sacB (8) contains the Red operon expressed under the control of the arabinose inducible pBAD promoter and the sacB gene that is necessary to cure the plasmid (8, 9).

Strain V674 was produced from strain IP32953p by deletion of the HPI, yopK and psaA, as described in (1).

Construction of V674TnF1 and Verification of F1 Capsule Production

Cloning of the Caf Locus:

Cloning of the *Y. pestis* caf locus in the mini transposon Tn7 was performed as follows: The 5 kb caf locus that encodes the F1 capsule of *Y. pestis* was amplified by PCR with primers A (5'-ATAAGAATGAATTCGTGACTGAT-CAAATATGTTGG-3'; SEQ ID NO: 1) and B (5'-CGT-TAGGGCCCGTCAGTCTTGCTATCAATGC-3'; SEQ ID NO: 2), which add an ApaI and EcoRI site at the extremities of the locus. The PCR product was ligated to the corresponding sites in the mini transposon Tn7 carried by the pUC18R6KTn7-$Cm^R$ plasmid (FIG. 1), generating plasmid pUC18R6KTn7-Cm$^R$-caf. The presence of the caf locus was verified by PCR using primers 157A (5'-CAGGAAC-CACTAGCACATC-3'; SEQ ID NO: 3) and 157B (5'-CCCCCACAAGGTTCTCAC-3'; SEQ ID NO: 4) internal to the caf1 gene.

Insertion of the Caf Locus into the *Y. pseudotuberculosis* Chromosome

To insert the caf locus into the *Y. pseudotuberculosis* V674 chromosome we used the mini Tn7 tool (2). Plasmids pUC18R6KTn7-Cm$^R$-caf and pTNS2 (transposase provider) were used together to electroporate the *Y. pseudotuberculosis* vaccine strain V674 (1), and the transposants were selected on LB agar plates containing Chloramphenicol.

The presence of the transposon that contains the caf locus (named "Mini Tn7-caf-Cm$^R$ transposon", FIG. 2) was verified by PCR, using two pairs of primers: 744 (5'-CACAG-CATAACTGGACTGATTTC-3'; SEQ ID NO: 5) and 747 (5'-GCTATACGTGTTTGCTGATCAAGATG-3'; SEQ ID NO: 6) for the left junction, and 745 (5'-ATTAGCTTAC-GACGCTACACCC-3'; SEQ ID NO: 7) and 746 (5'-ACGC-CACCGGAAGAACCGATACCT-3'; SEQ ID NO: 8) for the right junction. The recombinant *Y. pseudotuberculosis* strain that contains the Tn7-caf-Cm$^R$ region in its chromosome was named V674TnF1.

Since the transposase-encoding plasmid is not harbored by the recombinant V674TnF1, excision of the Tn7-caf-Cm$^R$ region by transposition does not occur.

Verification of F1 Capsule Production

Figure 3:
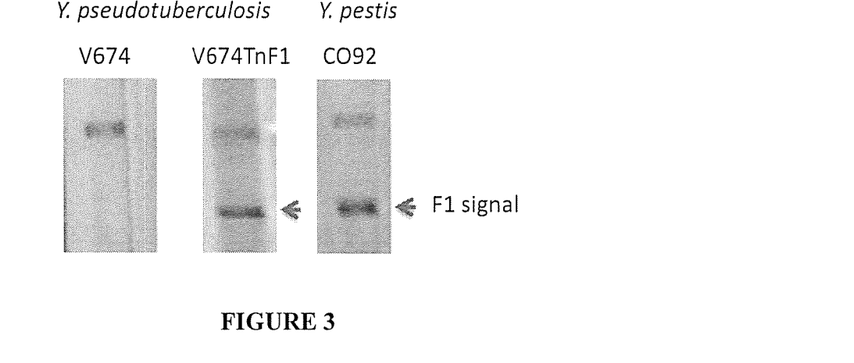
FIG. 3: Detection of the production of *Y. pestis* F1 by an attenuated *Y. pseudotuberculosis* strain, in which the caf operon has been inserted into the genome (strain V674TnF1). V674 is the parental strain that does not possess a caf operon. CO92 is the *Y. pestis* strain used for the cloning of the caf operon.

To estimate the F1 capsule production by the recombinant V674TnF1 vaccine, the strain was grown at 37° C. in LB broth, and a F1 dipstick test (3) was performed on cell suspensions. As shown on FIG. 3, a band at the same position as the positive *Y. pestis* control was observed with CO92 (positive control) whereas no signal was detected with the V674 parental strain (negative control), thus indicating that V674TnF1 synthesizes the F1 capsule.

Figure 4:
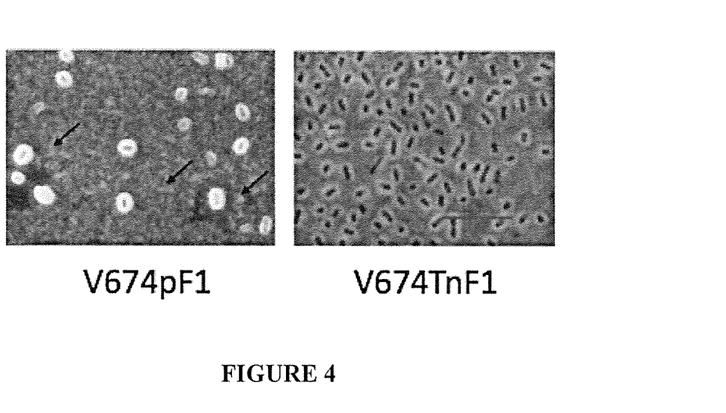
FIG. 4: Detection of F1 capsules around attenuated *Y. pseudotuberculosis* cells, which comprise the *Y. pestis* caf operon either on a plasmid (*Y. pseudotuberculosis* strain V674pF1; left-hand panel) or inserted into the chromosome (*Y. pseudotuberculosis* V674TnF1; right-hand panel). In V674pF1, numerous bacteria are not surrounded by a capsule (some examples are shown with an arrow), while all V674TnF1 cells are encapsulated.

To further visualize the F1 capsule, we examined microscopically the V674TnF1 strain grown at 37° C. Exclusion of India ink around V674TnF1 bacterial cells confirmed the presence of the capsule (FIG. 4).

Furthermore, all bacterial cells were surrounded by a halo, indicating that, in contrast to V674 pF1, all bacteria produced the F1 capsule. After two subcultures in LB, all bacterial cells continued to produce F1. Therefore, the synthesis of F1 is much more stable in V674TnF1 than in V674pF1.

Attenuation of Virulence

The V674 strain used to construct V674pF1 and V674TnF1 had been modified to attenuate its virulence by deletion of 3 virulence factors (the High Pathogenicity Island, the pH6 Ag/PsaA pilus, and the YopK factor) by genetic engineering (1).

The virulence of the V674pF1 and V674TnF1 strains was tested after intragastric administration. In both cases, the $LD_{50}$ was $>10^{10}$ CFU, demonstrating a very strong attenuation of virulence. However, we noticed occasional mouse deaths after intragastric vaccination, which were not related to the vaccine dose used (see Table 1 below), and which most likely resulted from accidental lesions caused by the intragastric canulla used to administrate the vaccine.

The virulence of the V674TnF1 strain was also tested after subcutaneous (SC) administration. After subcutaneous injection of doses of the V674TnF1 strain up to $10^9$ CFU, no deaths were observed Skin papules were observed in all mice vaccinated with $10^9$ CFU of V674TnF1, in about 50% at $10^8$ CFU and <10% at $10^7$ CFU.

TABLE 1

| Inoculation doses (CFU) | % mortality (number of deaths/total inoculated mice) | | |
|---|---|---|---|
| | V674pF1 Intragastric | V674TnF1 Intragastric | V674TnF1 Subcutaneous |
| $10^7$ | 0% (0/16) | 4.1% (1/24) | 0% (0/16) |
| $10^8$ | 2% (1/48) | 3.6% (2/55) | 0% (0/13) |
| $10^9$ | 0% (0/56) | 2.5% (1/40) | 0% (0/8) |
| $10^{10}$ | 0% (0/8) | 0% (0/8) | Not done |

Persistence of V674TnF1 in Mice Upon Oral Inoculation

Figure 5A:
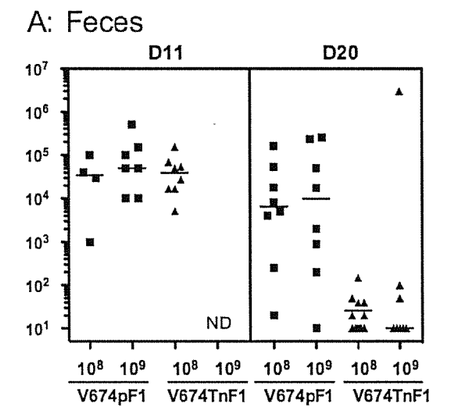
FIGS. 5A, 5B and 5C: Attenuated *Y. pseudotuberculosis* cells, which carry the *Y. pestis* caf operon, persist in the intestinal flora (FIG. 5A), the Peyer's patches (FIG. 5B), and the spleen (FIG. 5C) of mice vaccinated orally with $10^8$ or $10^9$ CFU.

After oral inoculation of either $10^8$ or $10^9$ CFU, V674TnF1 bacterial cells were detected in the feces of only 3 out of 8 mice on D20, and only with the $10^9$ CFU vaccine dose (FIG. 5A), indicating a relatively rapid clearance of the vaccine from the gut lumen.

Figure 5B:
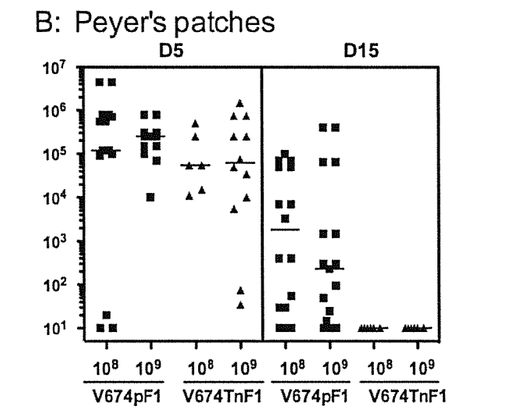
Figure 5C:
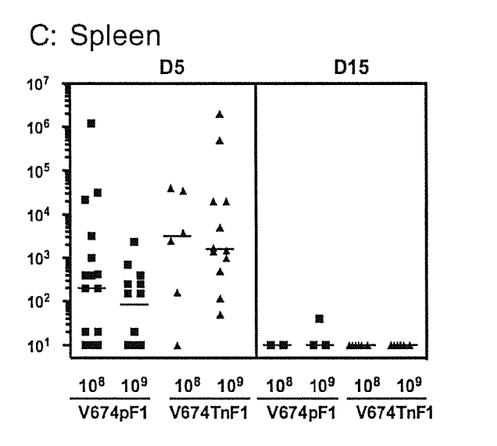

In Peyer's patches and the spleen, V674TnF1 was detected after 5 days, but was cleared after 15 days (FIGS. 5B and 5C), regardless of the dose administered.

In contrast, V674pF1 bacterial cells were still detectable in Peyer's patches and in the spleen of 1/5 mouse on D15, indicating that V674TnF1 is more rapidly cleared from the vaccinated animals than the V674pF1 strain.

Altogether, our observations demonstrate that V674TnF1 administered orally is able to colonize the gut, Peyer's patches and spleen, but this colonization is only transient, and bacteria are cleared from deep organs before D15.

Protection Conferred Against Bubonic and Pneumonic Forms of Plague

To evaluate and compare the protective efficacy of V674pF1 and V674TnF1, mice were vaccinated and were infected one month later either intranasally (IN, pneumonic plague) or subcutaneously (SC, bubonic plague) with the fully virulent *Y. pestis* strain CO92 (4). For each infection route, two lethal challenges of CO92 were tested, with a moderate and a high dose of the fully virulent *Y. pestis* strain CO92.

TABLE 2

| | Moderate challenge | | Severe challenge | |
|---|---|---|---|---|
| | CFU | x $LD_{50}$ | CFU | x $LD_{50}$ |
| IN | $10^5$ | 33 | $10^7$ | 3,300 |
| SC | $10^3$ | 100 | $10^5$ | 10,000 |

Oral Vaccination

Figure 6A:
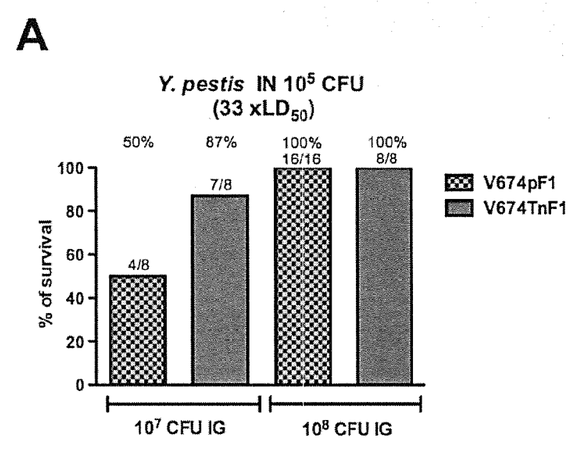
FIGS. 6A and 6B: Protection conferred by a single oral vaccination with attenuated *Y. pseudotuberculosis* cells, which carry the *Y. pestis* caf operon either on a plasmid (strain V674pF1) or inserted into the chromosome (strain V674TnF1), against pneumonic plague following a moderate (FIG. 6A) or a severe (FIG. 6B) intranasal challenge with *Y. pestis* (pneumonic plague).

—Protection Against Pneumonic Plague:

A dose of $10^7$ CFU of either V674pF1 or V674TnF1 strain did not confer full protection against a moderate IN challenge with *Y. pestis* (FIG. 6A).

In contrast, a dose of $10^8$ CFU of either strain protected 100% of the animals against a similar challenge (FIG. 6A).

Figure 6B:
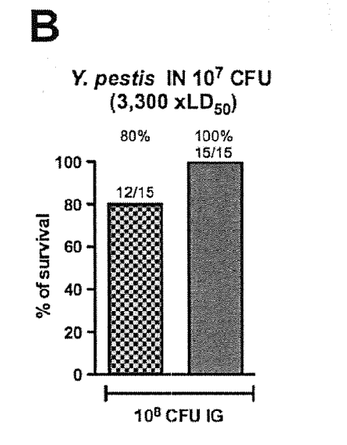

Since the $10^8$ CFU dose was effective, a severe bacterial challenge was tested (FIG. 6B). Following this high challenge, only 80% of the mice vaccinated with V674pF1 survived, while all animals vaccinated with V674TnF1 survived.

Our results thus show the higher protective effect of V674TnF1 over V674pF1 and indicate that a single oral dose of V674TnF1 is sufficient to fully protect against pneumonic plague, even after exposure to high *Y. pestis* loads.

Figure 7A:
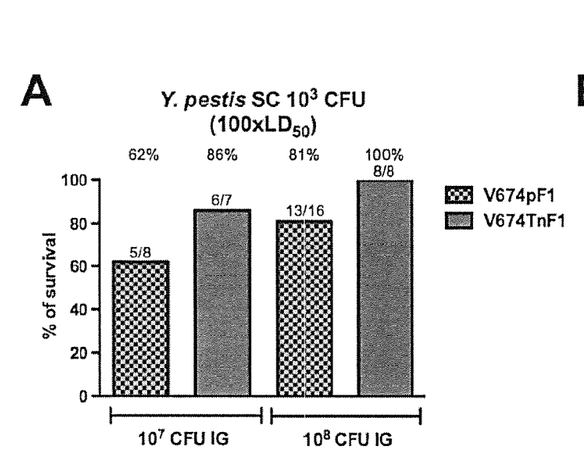
FIGS. 7A and 7B: Protection conferred by a single oral vaccination with attenuated *Y. pseudotuberculosis* cells, which carry the *Y. pestis* caf operon either on a plasmid (strain V674pF1) or inserted into the chromosome (strain V674TnF1), against bubonic plague following a moderate (A) or a severe (B) subcutaneous challenge with *Y. pestis* (bubonic plague).

—Protection Against Bubonic Plague:

A single oral administration of $10^7$ CFU of V674pF1 or V674TnF1 was not sufficient to obtain 100% protection against a moderate SC challenge with *Y. pestis* (FIG. 7A).

At a dose of $10^8$ CFU, V674pF1 conferred 86% protection, while V674TnF1 protected 100% of the vaccinated mice (FIG. 7A).

Figure 7B:
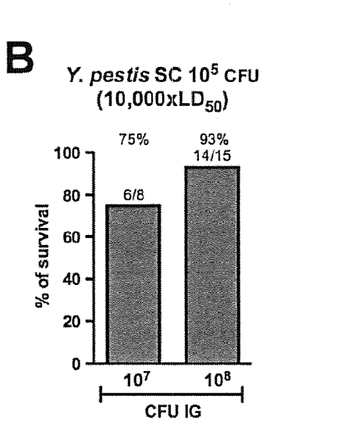

When the challenge dose was increased to $10,000 \times LD_{50}$, a single oral administration of $10^8$ CFU of V674TnF1 still protected 93% of the animals (FIG. 7B).

V674TnF1 is thus more effective than V674pF1 at protecting against bubonic plague.

Altogether, our results demonstrate that a single oral inoculation of $10^8$ CFU of V674TnF1 is very efficient at vaccinating mice against both pneumonic and bubonic plague, even when the animals are challenged with very high doses of the fully virulent *Y. pestis* strain CO92.

Subcutaneous Vaccination

Since one of the 15 mice vaccinated with V674TnF1 did not survive after a severe SC challenge, we wondered whether it would be possible to increase even further the protection by using another route of vaccination.

—Protection Against Pneumonic Plague after SC Vaccination

Figure 8:
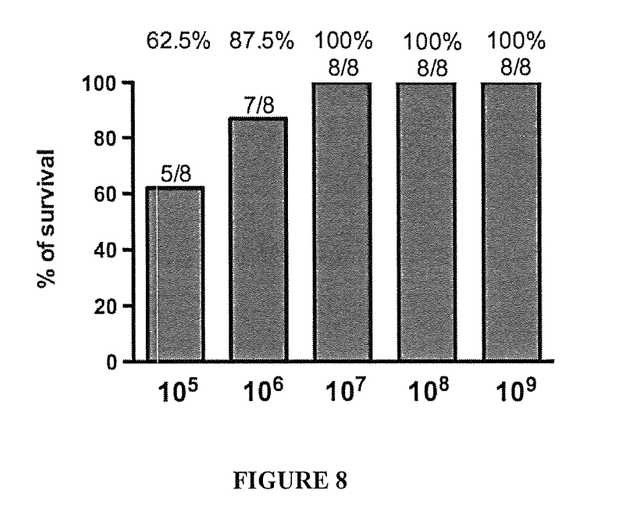
FIG. 8: Protection conferred by a single subcutaneous inoculation of $10^7$ or $10^8$ CFU of attenuated *Y. pseudotuberculosis* cells, wherein the *Y. pestis* caf operon has been inserted into the chromosome (strain V674TnF1), against bubonic plague (subcutaneous infection) with a severe challenge of *Y. pestis* (strain CO92).

To test the protective efficacy of an SC inoculation of V674TnF1, a single vaccine dose of $10^5$ to $10^9$ CFU was injected and the animals were challenged with a high IN inoculum ($10^7$ CFU=$3,300 \times LD_{50}$) of *Y. pestis* CO92. Full protection was obtained with vaccine doses of $10^7$ CFU and higher (FIG. 8).

—Protection Against Bubonic Plague after SC Vaccination

The protection conferred by a single SC injection of V674TnF1 ($10^7$ or $10^8$ CFU) against bubonic plague (severe challenge: $10,000 \times LD_{50}$) was then evaluated.

Figure 9:
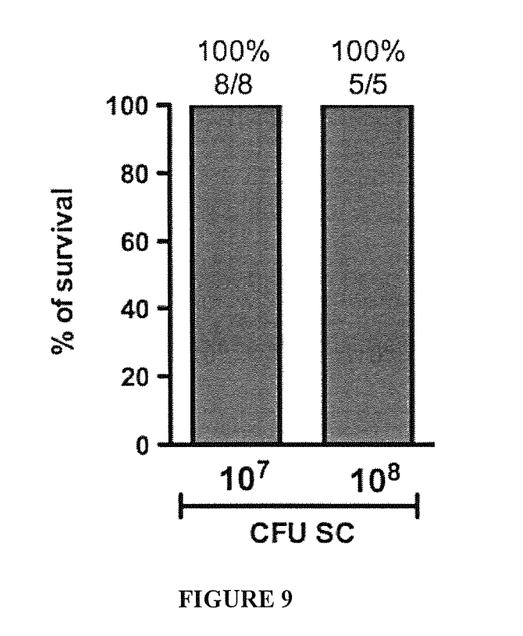
FIG. 9: Protection conferred by a single subcutaneous inoculation of various doses of attenuated *Y. pseudotuberculosis* cells, wherein the *Y. pestis* caf operon has been inserted into the chromosome (strain V674TnF1), against pneumonic plague (intranasal infection) with a severe challenge of *Y. pestis* (strain CO92).

A single vaccination with either dose protected 100% of the animals against a severe challenge dose ($10,000 \times LD_{50}$) of *Y. pestis* CO92 administered SC (FIG. 9), indicating an efficiency even higher than that of the oral vaccination against bubonic plague.

CONCLUSIONS

The V674TnF1 *Y. pseudotuberculosis* strain, in which the operon encoding the *Y. pestis* capsular antigen F1 has been inserted into the chromosome, is an efficient vaccine against both bubonic plague and pneumonic plague.

The V674TnF1 *Y. pseudotuberculosis* strain notably has the following advantages:

genetic stability: V674TnF1 is a *Y. pseudotuberculosis* strain, whose genome is much more stable than that of *Y. pestis*;

innocuity: V674TnF1 is highly attenuated, due to the irreversible deletion of three genes essential to distinct virulence mechanisms: adhesion (pH6 Ag/PsaA), iron capture (HPI), secretion of Yop toxins (YopK);

molecular diversity: as a live whole cell vaccine, it offers a high antigenic complexity, which guarantees a response against a broad range of antigenic targets; antigens are in their native form, adequately processed, and produced de novo as long as the bacteria persist;

easy manufacturing: once developed and validated, live vaccines do not require sophisticated equipments and techniques to be produced;

immunogenicity: adjuvant is not required, since bacterial antigens (LPS and other pathogen associated signatures) trigger the innate immune system; in addition to antigens common to *Y. pestis* and *Y. pseudotuberculosis*, V674TnF1 stably produces the F1 capsule, which is a major vaccine target against *Y. pestis*;

single dose administration: this is a major advantage as it greatly facilitates vaccination campaigns and allows a rapid protection;

vaccination possible by two routes: depending on the context, an SC or oral route of vaccination may be preferred.

Furthermore, V674TnF1 has very high vaccine efficacy. Animals vaccinated with V674TnF1 are fully protected against both bubonic and pneumonic plague, even when exposed to very high doses of the plague *bacillus*.

In contrast, V674pF1 achieves a lower vaccine efficacy, more particularly with respect to bubonic plague.

To our knowledge, the level of protection against bubonic and pneumonic plague conferred by a single dose of the V674TnF1 vaccine is one of the most, and probably the most efficient ever reported.

We further observed that V674TnF1 surprisingly is more rapidly cleared from the gut of the vaccinated animals than V674pF1, and that subcutaneous or oral administration of V674TnF1 are efficient route of administration depending on the intended use in prevention or urgent treatment.

BIBLIOGRAPHIC REFERENCES

1. Derbise, A., Cerda Marin, A., Ave, P., Blisnick, T., Huerre, M., Carniel, E., and Demeure, C. E. (2012) An encapsulated *Yersinia pseudotuberculosis* is a highly efficient vaccine against pneumonic plague. *PLoS Negl Trop Dis* 6, e1528
2. Choi, K. H., Gaynor, J. B., White, K. G., Lopez, C., Bosio, C. M., Karkhoff-Schweizer, R. R., and Schweizer, H. P. (2005) A Tn7-based broad-range bacterial cloning and expression system. *Nat Methods* 2, 443-448
3. Chanteau, S., Rahalison, L., Ralafiarisoa, L., Foulon, J., Ratsitorahina, M., Ratsifasoamanana, L., Carniel, E., and Nato, A. (2003) Development and testing of a rapid diagnostic test for bubonic and pneumonic plague. *Lancet* 361, 211-216
4. Chain, P. S., Cannel, E., Larimer, F. W., Lamerdin, J., Stoutland, P. O., Regala, W. M., Georgescu, A. M., Vergez, L. M., Land, M. L., Motin, V. L., Brubaker, R. R., Fowler, J., Hinnebusch, J., Marceau, M., Medigue, C., Simonet, M., Chenal-Francisque, V., Souza, B., Dacheux, D., Elliott, J. M., Derbise, A., Hauser, L. J., and Garcia, E. (2004) Insights into the evolution of *Yersinia pestis* through whole-genome comparison with *Yersinia pseudotuberculosis*. *Procedings of the National Academy of Sciences of the United States of America* 101, 13826-13831
5. Parkhill, J., Wren, B. W., Thomson, N. R., Holden, M. T. G., et al. (2001) Genome sequence of *Yersinia pestis*, the causative agent of plague. Nature 413: 523-527
6. Chain, P., Regala, W., Mariero, L., Souza, B., Elliott, J., et al. (2002) Whole genome sequencing of *Yersinia pseudotuberculosis*: Examining pathogen evolution among the recently emerged *Yersinia*. Abstracts of the General Meeting of the American Society for Microbiology 102
7. Pouillot, F., Derbise, A., Kukkonen, M., Foulon, J., Korhonen, T. K., et al. (2005) Evaluation of O-antigen inactivation on Pla activity and virulence of *Yersinia pseudotuberculosis* harbouring the pPla plasmid. Microbiology 151: 3759-3768

8. Derbise, A., Lesic, B., Dacheux, D., Ghigo, J. M., Carniel, E. (2003) A rapid and simple method for inactivating chromosomal genes in *Yersinia*. FEMS Immunol Med Microbiol 38(2):113-116.
9. Datsenko, K., A., Wanner, B. L. (2000) One-step inactivation of chromosomal genes in *Escherichia coli* K-12 using PCR products. Proc. Natl. Acad. Sci. U.S.A. 97(12): 6640-6645.
10. Grinter, N. J. (1983). A broad-host-range cloning vector transposable to various replicons. Gene 21: 133-143.
11. Barry, G. F. (1986). Permanent insertion of foreign genes into the chromosome of soil bacteria. Bio/Technology 4: 446-449.
12. Bao, Y., D. P. Lies, H. FU, and G. P. Roberts (1991). An improved Tn7-based system for the single-copy insertion of cloned genes into chromosomes of Gram-negative bacteria. Gene 109: 167-168.
13. Højberg, O., U. Schnider, H. V. Winteler, J. Sørensen, and D. Haas (1999). Oxygen-sensing reporter strain of *Pseudomonas fluorescens* for monitoring the distribution of low-oxygen habitats in soil. Appl. Environ. Microbiol. 65: 4085-4093.
14. Koch, B., L. E. Jensen, and O. Nybroe (2001). A panel of Tn7-based vectors for insertion of the gfp marker gene or for delivery of cloned DNA into Gram-negative bacteria at a neutral chromosomal site. J. Microbiol. Meth. 45: 187-195.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09492524B2). An electronic copy of the "Sequence Listing" will also be available from the USPTO upon request and payment of the fee set forth in 37 CFR 1.19(b)(3).

The invention claimed is:

1. A genetically attenuated *Yersinia pseudotuberculosis* cell, wherein one or more genes selected from HPI, yopK and psaA are deleted or inactivated, and wherein nucleic acid coding for expression of at least one *Yersinia pestis* Caf1 polypeptide at the surface of said *Y. pseudotuberculosis* cell is integrated into the chromosome of said *Y. pseudotuberculosis* cell.

2. The genetically attenuated *Y. pseudotuberculosis* cell of claim 1, which is a live cell or a killed cell.

3. The genetically attenuated *Y. pseudotuberculosis* cell of claim 2, which expresses said at least one surface-expressed *Y. pestis* Caf1 in oligomeric form.

4. The genetically attenuated *Y. pseudotuberculosis* cell of claim 1, which expresses the *Y. pestis* F1 protein at its surface.

5. The genetically attenuated *Y. pseudotuberculosis* cell of claim 1, which is surrounded by a *Y. pestis* capsule.

6. The genetically attenuated *Yersinia pseudotuberculosis* cell of claim 1, which derives from a cell of the *Y. pseudotuberculosis* IP 32953 strain, the chromosomal sequence of which is the sequence available under accession number NC_006155 (SEQ ID NO: 19), by:
 deletion or inactivation of one or more genes selected from HPI, yopK and psaA, and by
 chromosomal insertion of nucleic acid coding for expression of at least one *Yersinia pestis* Caf1 polypeptide at the surface of said *Y. pseudotuberculosis* cell.

7. The genetically attenuated *Yersinia pseudotuberculosis* cell of claim 1, wherein at least one transposon carrying the caf operon is integrated in the chromosome of said *Y. pseudotuberculosis* cell.

8. A composition comprising a plurality of genetically attenuated *Yersinia pseudotuberculosis* cells according to claim 1.

9. An immunogenic composition, comprising an immunogenically effective amount of live genetically attenuated *Yersinia pseudotuberculosis* cells;
 wherein the HPI gene is deleted or inactivated in the *Yersinia pseudotuberculosis* cells, the yopK gene is deleted or inactivated in the *Yersinia pseudotuberculosis* cells, and the psaA gene is deleted or inactivated in the *Yersinia pseudotuberculosis* cells; and
 wherein nucleic acid coding for expression of at least one *Yersinia pestis* Caf1 polypeptide at the surface of said *Y. pseudotuberculosis* cell is integrated into the chromosome of said *Y. pseudotuberculosis* cell.

10. The immunogenic composition of claim 9, which comprises a single unit dose of the live genetically attenuated *Yersinia pseudotuberculosis* cells.

11. A method for treating a *Y. pestis* infection in a mammal, which comprises administering an effective amount of the immunogenic composition of claim 9 to said mammal having a *Y. pestis* infection to thereby treat the *Y. pestis* infection in said mammal.

12. The method of claim 11, wherein said mammal is a human.

13. A method of immunizing a mammal against *Y. pestis* infection, comprising administering an effective immunizing amount of the immunogenic composition of claim 9 to said mammal.

14. The method of claim 13, wherein said mammal is a human.

15. A vaccine comprising an immunizing amount of live genetically attenuated *Yersinia pseudotuberculosis* cells;
 wherein the HPI gene is deleted or inactivated in the *Yersinia pseudotuberculosis* cells, the yopK gene is deleted or inactivated in the *Yersinia pseudotuberculosis* cells, and the psaA gene is deleted or inactivated in the *Yersinia pseudotuberculosis* cells; and
 wherein nucleic acid coding for expression of at least one *Yersinia pestis* Caf1 polypeptide at the surface of said *Y. pseudotuberculosis* cell is integrated into the chromosome of said *Y. pseudotuberculosis* cell.

16. The vaccine of claim 15, which comprises a single unit dose of the live genetically attenuated *Yersinia pseudotuberculosis* cells.

17. The vaccine of claim 15, which is formulated for oral administration.

18. The vaccine of claim 15, which is formulated for subcutaneous, intradermal, intranasal, or intramuscular administration.

19. The vaccine of claim 15, which is formulated for non-oral administration.

* * * * *